United States Patent [19]

Lange et al.

[11] 4,048,169

[45] Sept. 13, 1977

[54] 1,3-BIS-(β-ETHYLHEXYL)-5-NITRO-5-METHYL-HEXAHYDROPYRIMIDINE-NAPHTHALENE-1,5-DISULPHONATE

[75] Inventors: Fritz-Walter Lange, Gauting; Gert Haffner, Laupheim; Jens Müller, Gauting, all of Germany

[73] Assignee: MEDITEST Institut fur medizinisch pharmazeutische Untersuchungen GmbH, Neu-Ulm, Germany

[21] Appl. No.: 739,427

[22] Filed: Nov. 8, 1976

Related U.S. Application Data

[62] Division of Ser. No. 544,217, Jan. 27, 1975, Pat. No. 4,010,160.

[51] Int. Cl.$^2$ ............................................ C07D 239/04
[52] U.S. Cl. ................................................. 260/251 R
[58] Field of Search ..................................... 260/251 R

[56] References Cited

U.S. PATENT DOCUMENTS 3,749,721   7/1973   Herrmann et al. ........... 260/256.4 H

OTHER PUBLICATIONS

Senkus, *J. Amer. Chem. Soc.*, vol. 68 (1946) pp. 1611–1613.

*Primary Examiner*—Paul M. Coughlan, Jr.
*Attorney, Agent, or Firm*—Anthony P. DeLio

[57] ABSTRACT

The process provided for the production of high-purity 1,3-bis-(β-ethylhexyl)-5-amino-5-methyl-hexahydropyrimidine, also known as hexetidin, by reacting 1,3-bis-(β-ethylhexyl)-5-nitro-5-methyl-hexahydropyrimidine with naphthalene-1,5-disulphonic acid in a solvent to selectively precipitate the novel intermediate compound 1,3-bis-(β-ethylhexyl)-5-nitro-5-methyl-hexahydropyrimidine-naphthalene-1,5-disulphonate, which is separated off, treated with aqueous alkali to produce 1,3-bis-(β-ethylhexyl)-5-nitro-5-methyl-hexahydropyrimidine, and subsequently hydrogenated to produce high-purity hexetidin.

1 Claim, No Drawings

1,3-BIS-(β-ETHYLHEXYL)-5-NITRO-5-METHYL-HEXAHYDROPYRIMIDINE-NAPHTHALENE-1,5-DISULPHONATE

This is a division, of application Ser. No. 544,217, filed Jan. 27, 1975, U.S. Pat. No. 4,010,160.

The invention relates to an industrially practicable process for the manufacture of high-purity 1,3-bis(β-ethylhexyl)-5-amino-5-methyl-hexahydropyrimidine of the formula

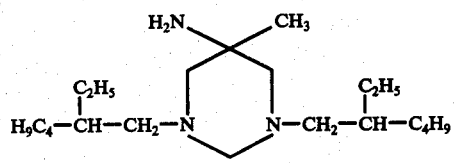

which is also known by the name of hexetidin and in view of its antimicrobial activity is used as an antiseptic and insecticide.

From M. Senkus, Journal of Americam Chemical Society, 68, 1611 –1613 (1946), it is known to manufacture 5-nitrohexahydropyrimidine by reaction of an aliphatic amine with formaldehyde followed by reaction with an aliphatic nitro compound. These 5-nitro-hexahydropyrimidines are then hydrogenated in methanolic solution using raney nickel as catalyst, whereby the 5-amino-hexahydropyrimidines are formed.

Similarly to this process described by Senkus, the 1,3-bis-(β-ethylhexyl)-5-nitro-5-methyl-hexahydropyrimidine can be obtained by reaction of 2-ethylhexylamine with formaldehyde followed by reaction with nitroethane. The oily reaction product, which is yellowish in colour, contains 1,3-bis-(β-ethylhexyl)-5-nitro-5-methyl-hexahydropyrimidine, which can always only be obtained as a crude product of 70 to 80% in a mixture with impurities which are present at 20 to 30% in addition to the main product. As by-products there have chiefly been observed $N_1,N_3$-bis-(ethylhexyl)-2-nitro-2-methyl-1,3-propanediamine of the formual

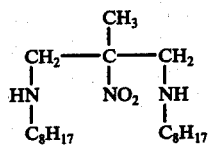

and small quantities of other substances. This process has the disadvantage that the mixture of main product and by-product cannot be separated by distillation, because the substances have very high boiling points lying very close to one another.

The highly impure mixture, which contains the desired nitro compound only up to 70 to 80% is then hydrogenated in an autoclave at 100 to 120 atmospheres overpressure in methanolic solution using raney nickel as catalyst. After blowing off the hydrogen, the contents of the autoclave after being freed from the catalyst by filtration are freed of water and organic solvents in a vacuum at a maximum temperature of 50° C. The product thus obtained is a crude hexetidin and consequently at the most 70% and usually only 60% hexetidin and consequently unsuitable for use in pharmaceutical preparations. There has therefore already been proposed a purification process, in order to obtain the synthesized crude product in pharmaceutical quality.

There is also known another process for the manufacture of hexetidin using the Schmidt reaction (Kawahara, Chem. Abstr. 58, 1963, column 13968 g), though this has no significance for industrial purposes since it includes dangerous process steps and likewise leads to a highly impure hexetidin.

From German Offenlegungsschrift 2011078 there is known a process which is based on the fact that from solutions of the crude hexetidin obtained in known manner the not-readily-soluble hexetidin-naphthalene-1,5-disulphonate is selectively separated out by means of naphthalene-1,5-disulphonic acid. Under the conditions of this process the secondary constituents present in the form of impurities form substantially more readily soluble salts, which remain in solution during the precipitation of the disulphonate. For the solvents in this case there are used low aliphatic alcohols or mixtures thereof with water. Preferably, 60 to 70% isopropyl alcohol is suggested for this purpose.

By introduction into aqueous alkali, preferably into dilute soda lye, the hexetidin base is released from the salt; it may be taken up in a water-immiscible organic solvent. By careful distillation-off of the solvent in a vacuum, the pure hexetidin is then obtained. Although this process leads to a hexetidin which is largely free of by-products, it has the disadvantage that for manufacture of the 5-amino compound the whole crude hexetidin has to be hydrogenated. Also there is a danger that further impurities, hitherto absent, might be formed as a result of the action, proposed in German Offenlegungsschrift 2011078, of a strong acid and of a lye on the already hydrogenated, sensitive product.

The object of the invention is to avoid the above-mentioned disadvantages.

It has unexpectedly been found that 1,3-bis-(β-ethylhexyl)-5-amino-5-methyl-hexahydropyrimidine of pharmaceutical purity can be obtained by adding naphthalene-1,5-disulphonic acid in aqueous alcoholic solution to a mixture occurring in the case of the synthesis according to Senkus and containing 1,3-bis-(β-ethylhexyl)-5-nitro-5-methyl-hexahydropyrimidine up to about 60 to 80% and about 20 to 40% of other by-products, and by separating off the thus selectively precipitated 1,3-bis-(β-ethylhexyl)-5-nitro-5-methyl-hexahydropyrimidine-1,5-disulphonate. From this hitherto unknown compound of the following formula, which also has superior fungicidal and bactericidal properties,

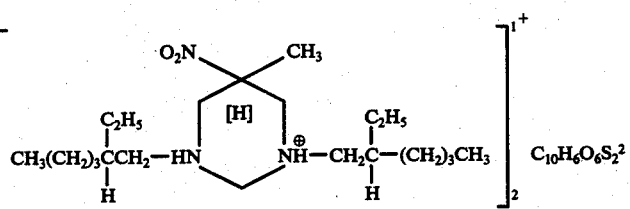

there can be obtained as a free base high-purity 1,3-bis-(β-ethylhexyl)-5-nitro-5-methyl-hexahydropyrimidine, from which 1,3-bis-(β-ethylhexyl)-5-amino-5-methyl-hexahydropyrimidine of pharmaceutical purity can be obtained by hydrogenation.

The new compound 1,3-bis-(β-ethylhexyl)-5-nitro-5-methyl-hexahydropyrimidine-naphthalene-1,5-disulphonate is obtained by reaction of crude 1,3-bis-(β-ethylhexyl)-5-nitro-5-methyl-hexahydropyrimidine with naphthalene-1,5-disulphonic acid in a solvent. Particularly suitable as the solvent are low aliphatic alcohols such as methyl alcohol, ethyl alcohol and especially isopropyl alcohol in mixtures thereof with water.

The mixture ratio of alcohol to water should advantageously be greater than 1:1, preferably 2:1 to 5:1.

The $N_1,N_3$-bis-(ethylhexyl)-2-nitro-2-methyl-propanediamine-1,5-disulphonate, which is the main impurity, is dissolved. Also the other accompanying substances are soluble in the aqueous/alcoholic medium.

The selectively precipitated 1,3-bis-(β-ethylhexyl)-5-nitro-5-methyl-hexahydropyrimidine-naphthalene-1,5-disulphonate is centrifuged off, washed with aqueous isopropyl alcohol, preferably 80% isopropyl alcohol, and dried at 50° to 60° C. The white crystals, which occur in very high yields, have a purity of more than 99%. The nitro base is separated from the salt by addition to aqueous alkali, preferably dilute soda lye or potash lye. Suitable for taking up the separated nitro base are water-immiscible solvents such as butyl alcohol, acetic acid ethyl ester, petroleum either and chlorinated hydrocarbons, preferably methylene chloride. It has been found that methylene chloride is particularly suitable for taking up the nitro base because, in advantageous contrast to petroleum ether, it can easily be removed from the nitro base without great application of heat, whereby there is formed a particularly pure 1,3-bis-(β-ethylhexyl)-5-nitro-5-methyl-hexahydropyrimidine of light colour. A further advantage of the use of methylene chloride lies in that less than half the quantity of this solvent is required for taking up the hexetidin compared to the necessary quantity of petroleum ether.

The new intermediate product is then hydrogenated in known manner to form hexetidin of pharmaceutical purity.

With the aid of this new compound, the rest of the synthesization, i.e. the hydrogenation, does not proceed on mixed products as in the case of the known processes, but rather it is only one homogeneous substance which is treated. In this way, the starting quantity and working time of the treatment are reduced. Also there is obtained a hexetidin which from the economic point of view is purer than in the case of all the other known processes, since the separation of the by-products which in the known methods are also hydrogenated is an extremely elaborate operation.

The 1,3-bis-(β-ethylhexyl)-5-nitro-5-methyl-hexahydropyrimidine exhibits completely different properties compared to hexetidin. Thus, for example, this nitro compound does not form a salt with oxalic acid, but merely an oily liquid. For selective purification, however, the formation of salt in the form of solids is necessary, so that these can be separated from the impurities. In contrast to this, the oxalate of hexetidin is crystalline, since in this case the salt formation takes place by way of the primary amino group. Instead of the primary amino group in the 5-position of the hexetidin, which alone forms a salt despite the considerable supply of acid in accordance with German Offenlegungsschrift 2011078, the nitro compound used in accordance with the invention for purification purposes contains no primary amino group. It is therefore unexpected that with naphthalene-2,5-disulphonic acid it should nevertheless form a salt in the form of a precipitate. It is current teaching that tertiary amines are screened off in their basic centres by long-chain and (as in the case of the nitro compound) in particular by branched-chain radicals and are sterically hindered in such a way that they are not capable of salt formation. Also, the nitro compound is greatly reduced in its basicity by the long-chain aliphatic radicals.

It was thus necessary to overcome a series of generally held prejudices in order to arrive at the process in accordance with the invention.

In what follows the invention will be described in more detail with reference to examples.

EXAMPLE 1

18.480 kg of crude 1,3-bis-(β-ethylhexyl)-5-nitro-5-methyl-hexahydropyrimidine (50.0 mol) with a content of 70% are dissolved in 40 liters isopropyl alcohol, and heated to 65°–70°. To this solution there is added while stirring a warm (65°–70°) solution of 9.22 kg (25 mol) 78% naphthalene-1,5-disulphonic acid in 50 liters isopropyl alcohol. There is added to this mixture while stirring 34 liters water at 60°–65°, and the whole is gradually cooled, while stirring, to 20°. The crystal sludge is centrifuged off and after washing with 50 liters of 60% isopropyl alcohol, dried at 60°.

Colourless crystals are obtained with a melting point of 149° C. The yield is 17.5 kg, which is 97% of the theoretical value on the basis of the quantity of 1,3-bis-(β-ethylhexyl)-5-nitro-5-methyl-hexahydropyrimidine contained in the starting mixture.

Summation formula: $C_{52} H_{92} N_6 O_{10} S_2$, molecular weight = 1,024.73;

CHNOS analysis: calculated: C: 60.95; H: 8.98; N: 8.20; O: 15.61; S: 6.26; found: C: 60.63; H: 9.04; N: 8.26; O: 15.54; S: 6.19.

EXAMPLE 2

1,848 g (5 mol) crude, 1,3-bis-(β-ethylhexyl)-5-nitro-5-methyl-hexahydropyrimidine with a content of 70% are dissolved in 3.6 liters of 96% ethyl alcohol. The solution is heated to 70°. To this solution there is added, while stirring a solution, heated to 65°, of 922 g (2.5 mol) 78% naphthalene-1,5-disulphonic acid in 8.4 liters of 60% ethyl alcohol, and the whole cooled gradually, while stirring, to 20° C. The crystal sludge is centrifuged off, washed with 5 liters 60% ethyl alcohol and dried at 60°. There are obtained colourless crystals with a melting point of 149° C. The yield is 1.714 kg, which is 95% of the theoretical value on the basis of the quantity of 1,3-bis-(β-ethylhexyl)-5-nitro-5-methyl-hexahydropyrimidine contained in the starting mixture.

EXAMPLE 3

17.5 kg of the 1,3-bis-(β-ethylhexyl)-5-nitro-5-methyl-hexahydropyrimidine-naphthalene-1,5-disulphonate obtained in Example 1, are added to a solution of 2.3 kg of sodium hydroxide in 100 liters of water. After the addition of 30 liters of methylene chloride the whole is stirred for about 10 minutes, until the salt has passed into solution. The organic phase is freed from residue by filtration and dried over sodium sulphate. After this solvent is completely distilled off under a vacuum, in which connection the slurry temperature should not exceed 60°.

Yield: 12.1 kg pure 1,3-bis-(β-ethylhexyl)-5-nitro-5-methylhexahydropyrimidine in the form of a light yellowish oil, corresponding to 93.5% of the theoretical value in relation to the crude 1,3-bis-(β-ethylhexyl)-5-nitro-5-methylhexahydropyrimidine used. Content of 1,3-bis-(β-ethylhexyl)-5-nitro-5-methylhexahydropyrimidine determined by gas chromatography: 99.4%. Summation formula: $C_{21}$, $H_{43}$ $N_3$ $O_2$, molecular weight: 369.6

CHNO analysis: calculated: C = 68.31; H = 11.65; N = 11.37; O = 8.67; found: C = 68.22; H = 11.72; N = 11.29; O = 8.73.

What we claim is:

1. 1,3-bis-(β-ethylhexyl)-5-nitro-5-methyl-hexahydropyrimidine-naphthalene-1,5-disulphonate of the formula

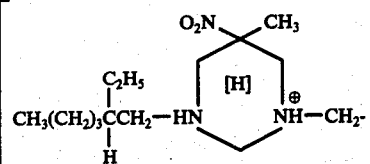
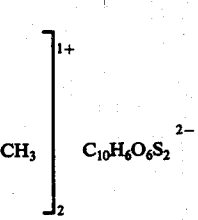

* * * * *

UNITED STATES PATENT AND TRADEMARK OFFICE
CERTIFICATE OF CORRECTION

PATENT NO. : 4,048,169
DATED : September 13, 1977
INVENTOR(S) : Fritz-Walter Lange, Gert Haffner and Jens Muller It is certified that error appears in the above-identified patent and that said Letters Patent are hereby corrected as shown below:

| | |
|---|---|
| Column 1, line 23 | "Americam" should read --American-- |
| Column 1, line 25 | "5-nitrohexahydropyrimidine" should read --5-nitro-hexahydropyrimidine-- |
| Column 2, line 5 | delete "and consequently" and substitute --containing-- |
| Column 3, line 31 | "either" should read --ether-- |
| Column 5, line 4 | "methylhexahydropyrimidine" should read --methyl-hexahydropyrimidine-- |
| Column 5, line 7 | "methylhexahydropyrimidine" should read --methyl-hexahydropyrimidine-- |
| Column 5, line 8 | "methylhexahydropyrimidine" should read --methyl-hexahydropyrimidine-- |

Signed and Sealed this

Sixth Day of December 1977

[SEAL]

Attest:

RUTH C. MASON
Attesting Officer

LUTRELLE F. PARKER
Acting Commissioner of Patents and Trademarks